United States Patent [19] [11] 3,994,781
Häggström [45] Nov. 30, 1976

[54] PROCESS FOR THE PRODUCTION OF PROTEIN

[75] Inventor: Lena Katarina Thorstensdotter Häggström, Lidingo, Sweden

[73] Assignee: AB Marabou, Sundbyberg, Sweden

[22] Filed: May 7, 1975

[21] Appl. No.: 575,176

Related U.S. Application Data

[63] Continuation of Ser. No. 336,180, Feb. 27, 1973, abandoned.

[30] Foreign Application Priority Data

Mar. 9, 1972 Sweden.............................. 2969/72

[52] U.S. Cl..................................... 195/49; 195/96
[51] Int. Cl.$^2$............................................ C12B 1/00
[58] Field of Search ................ 195/49, 96; 426/807

[56] References Cited
UNITED STATES PATENTS 3,755,082 8/1973 Terui et al............................ 195/49

OTHER PUBLICATIONS

Hammer et al., "Methane as a Carbon Source for the Production of Microbial Cells", Chemical Abstracts, vol. 68, p. 4661, Abs. No. 48292(c) (1968).

Foster et al., "A Methane–Dependent Coccus with Notes on Classification and Nomenclature of Obligate, Methane–Utilizing Bacteria," J. of Bacteriology, pp. 1924–1931, (1966).

*Primary Examiner*—A. Louis Monacell
*Assistant Examiner*—Thomas G. Wiseman
*Attorney, Agent, or Firm*—Brumbaugh, Graves, Donohue & Raymond

[57] ABSTRACT

A new microorganism, preliminarily called *Methylomonas methanolica* NRRL B-5458, is cultivated in a nutrient media containing methanol as sole source of carbon, the biomass being obtained containing protein of high quality and with an improved yield.

6 Claims, No Drawings

PROCESS FOR THE PRODUCTION OF PROTEIN

This is a continuation of application Ser. No. 336,180, filed Feb. 27, 1973, now abandoned.

The present invention relates to a new microorganism and particularly to a process for preparing protein of high quality and improved yield by means of a previously unknown microorganism, which oxidizes methanol, as well as protein thus prepared intended for animal and human consumption.

The following bacteria are known to produce protein when cultivated in nutrient solutions containing methanol, namely: Pseudomonas Methanica, Ps. sp ATCC No. 21 439, Ps. sp. ATCC No. 21 438, and Corynebacterium, sp ATCC No. 21 232, Co. sp ATCC No. 21 235 and Co. sp ATCC No. 21 236. These bacterias produce a biomass containing about 70% by weight of protein calculated on dry substance and about 5% by weight of fat calculated in the same way.

However, in order to increase the economic yield of the proces demands have been made to produce protein, at a yield which is considerably higher than that obtained by known strains.

It has now surprisingly been found that it is possible to meet this requirement according to the present invention by the discovery of a new, previously unknown microorganism, preliminarily called Methylomonas methanolica, NRRL No. B-5458. This is an obligate 1-carbon compound utilizing gram-negative, rod shaped bacterium, which is motile by means of a polar flagellum and which forms unpigmented macro colonies on solid substrates, the rods being $0.6 \times 1.6 \mu$.

On an electromicrograph the rods have rounded ends and appear alone or in pairs. In a standard cultivation slightly curved rods may be seen, too.

No apparent capsule can be observed in preparations stained with india ink, but on electronmicrographs of thin sections an unusual structure on the cell wall can be distinguished. Cells stained with sudan black show no affinity for this dye neither in logarithmic phase nor in stationary phase. Further the microorganism is catalase and oxidase positive.

Colonies on agar plates with an addition of methanol are white to pale yellow, rounded with entire edges, rather flat and give a partly transparent impression. After 1 day of cultivation the colonies are punctiform and after 6 days they have a diameter of 3 to 4 mm.

The optimum growth temperature is 30° C. The growth rate is markedly reduced at 15° C and 38° C. At 40° C the culture grows in the first transfer but fails to grow in subcultures thereof.

Optimum pH for growth in a liquid medium is 6.3 to 6.9, while the growth takes place in the total pH interval 5.3 to 8.5.

For maximal growth rate the methanol concentration should be kept below 1% by volume. At higher concentrations the growth rate and the yield is rapidly decreased and at a concentration exceeding 6% by volume no growth occurs.

Under the experimental conditions employed using a shaking table but no pH control or control of the substrate utilization the generation time is fairly constant between 1.5 to 1.8 hrs.

Ammonium chloride is by routine used as a source of nitrogen in nutrient solutions, but the microorganism utilizes nitrate, casamino acids and yeast extracts almost equally well, too. Nitrite and urea support growth, too but to a less extend and are inhibitory in concentrations above 0.1 g per liter of nutrient solution when cultivated in a medium containing nitrate and ammonium salts an analysable amount of nitrite is found.

Methanol is one of the hitherto known two sources of carbon, which the present microorganism, herein called Methylomonas methanolica, NRRL B-5458, is able to utilize for growth. Growth tests have been carried out on media containing as the only sources of carbon the following substances: methane; n-alkanols such as ethanol, propanol, butanol and pentanol; aldehydes such as formaldehyde, acetaldehyde, propionaldehyde, butyraldehyde and valeraldehyde; carboxylic acids such as formic acid, acetic acid, propionic acid, butyric acid and valeric acid; other organic acids such as citric acid, lactic acid, puruvic acid, succinic acid, fumaric acid, α-ketoglutaric acid and oxalic acid; sugars and related compounds such as glucose, fructose, lactose, sucrose, maltose, mannose, xylose, arabinose, glycerol, sorbitol, mannitol and inositol; complex media such as yeast extract, nutrient broth and peptone, casamino acids and indol, but no growth has been obtained at all.

The second source of carbon which the present microorganism seems to utilize is methyl amine. The microorganism is thus an obligate 1-carbon compound utilizer.

Media, which have been used by routine, have consisted of mineral salts having a composition and concentration in accordance with the following. Media consist of aqueous solutions of the mineral salts:

| | |
|---|---|
| $Na_2HPO_4$ | 600 mg/l |
| $KH_2PO_4$ | 400 |
| $MgSO_4 . 7 H_2O$ | 200 |
| $NH_4Cl$ | 800 |
| $FeCl_3 . 6 H_2O$ | 8.35 |
| $CaCl_2 . 2 H_2O$ | 0.33 |
| $ZnSO_4 . 7 H_2O$ | 0.09 |
| $CuSO_4 . 5 H_2O$ | 0.08 |
| $MnSO_4 . 4 H_2O$ | 0.08 |
| $CoCl_2 . 6 H_2O$ | 0.09 |

In those cases where methanol has been used, i.e. in all cases except for the source of carbon tests, it has been used in an amount of 0.3% by volume, pH of the medium being 6.7.

Solid substrated have been used on plates in such a way that Noble agar (Difco) has been added to the basic medium above in an amount of 1.5 % (weight by volume).

After autoclaving and cooling to 45° C methanol has been added in an amount of 0.5% by volume.

In growth tests using other sources of carbon than methanol 0.1% (weight by volume) of the source of carbon was added or less (0.05% as regards aldehydes) when inhibition was feared. If no growth appeared after 3 weeks of incubation, this was taken as evidence of inability of utilizing the source of carbon and thereby the substrate in question.

Samples from various sources such as soil from different places, water mud from ponds, compost earth, and sewage slude were used in the enrichment cultures. About 1 g of the sample was inoculated into 100 ml of liquid medium supplemented with 1% by volume of methanol and incubated statically at 30° C for 4 to 7 days. Serial dilutions were made before spreading the enrichments on methanol-agar plates. After incubation for 6 to 7 days single colonies were picked, serially diluted and spread on new plates. This procedure usually had to be repeated five times before a pure culture of an organism was obtained. Purity of the cultures was checked by microscopic examination of agar plates of living cell suspensions under phase-contrast, and of stained preparations.

Pure cultures were tested by routine for their ability to utilize methanol as source of carbon and energy when incubated in liquid media. To be considered as a true methanol-oxidizer a culture had to grow equally well in at least five serial subcultures with a total dilution of $10^{-10}$.

The found microorganism, herein preliminarily called Methylomonas methanolica, NRRL B-5458, in accordance with generally known and used nomenclature system has been used for the production of biomass in a batch-wise process. In this process the above mentioned liquid starting medium was used. Stock cultures of the strain were stored on solid medias in accordance with the foregoing.

In preparing inoculum for the biomass experiments, three successive transfers in shaking table flasks were made. The cells were harvested at the end of the logarithmic phase, centrifuged and resuspended in a small volume of fresh medium before they were used in an experiment.

For the fermentation a Biotec LP 600 fermentation unit was used, containing an automatic temperature control and a pH control and a stepless drive unit with magnetic coupling to the impeller. The fermentor (Biotec FL 103) has the following dimensions: Diameter 160 mm, height 200 mm and 4 baffles. The 8-blade impeller having a diameter of 70 mm was placed 70 mm from the bottom. The volume of the medium was 2500 ml and the speed of the stirrer was 900 rpm. At an aeration rate of 0.75 VVM the oxygen transfer rate was 150 mmoles of oxygen per liter and hour. pH was controlled by addition of 1 M $NH_4OH$. The concentration of methanol was controlled on basis of measurements of the amount of methanol in the outgoing air by means of a catalytic combustion principle.

Dissolved oxygen ($pO_2$) was analyzed by means of a probe according to Johnson, M. J., Borkowski, J., and Engblom, C., Biotechn. Bioeng. 6, 457 (1964). The values for $pO_2$, the amount of $NH_4OH$ added and the amount of methanol added were registered continuously. The cultivation temperature was 30° C.

The growth was followed by measurements of the dry weight and the optical density of the biomass obtained. Millipore membrane filters HAWP.04700 (HA 0.45 $\mu$, diameter 47 mm) were used for estimating the dry weight of the biomass. Fiters were dried at 105° C for 3 hrs. Optical density was measured in a Linson 3 colorimeter at wave length 620 nm.

Gas chromatography analyses were carried out in a Perkin-Elmer gas chromatograph, using a column temperature of 40° C, and helium as a carrier gas. Oxygen and nitrogen concentrations were measured directly, carbon dioxide being calculated as a residue. Determination of methanol in the medium was performed in a Pye gas chromatograph model 64 using a flame ionization detector, the column temperature being 135° C, whereby the column was packed with Porapak Q.

For the above mentioned microorganism the acceleration phase started during the second cultivation hour and lasted for 6 hrs. The logarithmic phase lasted 5 hrs and represented an increase of biomass from 0.3 to 3.0 g per liter. The declining phase continued until the 24th hour of cultivation. The stationary phase started at the biomass concentration 7.2 g/l. The values of biomass yield, growth rate and productivity of the logarithmic phase and the overall batch process are given in Table 1 below. The consumption of methanol is given in Table 2 below.

In logarithmic phase the consumption of methanol per unit of biomass is stable. In this phase the yield coefficient is the highest. In the declining phase the yield coefficient is subsequently decreased.

Table 1

|  | Logarithmic phase | Overall batch process |
|---|---|---|
| Biomass yield g/l | 3.0 | 7.2 |
| Maximal specific growth rate per hour | 0.510 | |
| Generation time (hrs) | 1.36 | |
| Productivity g/l, h | 0.84 | 0.30 |
| Maximal productivity g/l, h | >2.6 | 1.55 |
| Methanol consumption g per 1 g of biomass | 2.99 | 4.17 |
| Methanol yield coefficient g/g | 0.344 | 0.240 |
| Methanol carbon conversion % w/w | 42.77 | 30.70 |
| Oxygen consumption g per 1 g of biomass | 2.87 | 4.33 |
| Oxygen yield coefficient g/g | 0.348 | 0.231 |
| Maximal oxygen transfer rate needed, mmoles $O_2$/l, h | 138.90 | 138.90 |

In a continuous cultivation the maximal production is determined to 2.2 g of biomass per liter and hour, or higher.

Table 2

| Amount of biomass g/l | Methanol consumption g/l | Yield coefficient g $CH_3OH$/g of biomass |
|---|---|---|
| 0.5 | 2 | 0.25 |
| 1.0 | 3.7 | 0.33 |
| 2.0 | 6.3 | 0.33 |
| 3.0 | 9.0 | 0.33 |
| 4.0 | 12.2 | 0.33 |
| 5.0 | 15.2 | 0.28 |
| 6.0 | 19.0 | 0.18 |
| 6.5 | 22.5 | 0.125 |

The total composition of the biomass in the logarithmic phase is given in Table 3 below. The crude protein contents were 87.7% by weight. The methanol conversion was 42.76 %. The carbon recovery in the logarithmic phase was 98.5 ± 1.5%.

Table 3

The composition of elements of the biomass obtained using 0.3% by volume of methanol. The biomass was harvested at 1.3 g of biomass per liter of nutrient medium.

| Element | g/100 g of biomass, dry weight | Element | mg/100 g of biomass, dry weight |
|---|---|---|---|
| C | 47.90 | Fe | 115 |
| O | 23.75 | Cu | 33 |
| N | 13.95 | K | 30 |
| H | 7.20 | Na | 20 |
| P | 2.60 | Zn | 10 |
| S | 2.40 | Ca | 2 |
| Cl | 0.50 | Co | 0.50 |
| Mg | 0.28 | Mn | 0.28 |
|  |  | Mo | 0.20 |

-continued

| Element | g/100 g of biomass, dry weight | Element | mg/100 g of biomass, dry weight |
|---|---|---|---|
| Ashes | 4.80 | | |

By utilizing a methanol oxidizing bacteria such as the above mentioned *Methylomonas methanolica*, NRRL B-5458, the result is that the strain has a higher growth rate than other bacteria strains which are not obligate methanol-oxidizers, that the strain may be used for the detoxification of methanol containing substrates without simultaneously oxidizing other sources of carbon present in the substrate and that the strain is not able to utilize dead or lyzated cells for its growth. This latter fact gives advantages in a batch process in stationary phase. It is also probable that in this latter case less secondary products are obtained whereby a more pure and well defined protein should be obtained.

I claim:

1. A process for the preparation of protein of high quality and high yield, comprising aerobically cultivating in a nutrient solution containing methanol as a source of carbon, *Methylomonoas methanolica* NRRL B-5458, an obligate 1-carbon compound utilizing gram-negative, rod shaped bacterium, which is motile by means of a polar flagellum and which forms unpigmented macrocolonies on solid substrates, the rods being $0.6 \times 1.6 \mu$.

2. A process according to claim 1, characterized in that the amount of methanol present in the nutrient solution does not exceed 6% by volume.

3. A process according to claim 2, characterized in that the amount of methanol present in the nutrient solution suitably does not exceed 1% by volume.

4. A process according to claim 1, characterized in that the pH of the nutrient solution is 5.3 to 8.5.

5. A process according to claim 4, characterized in that the pH of the nutrient solution is 6.3 to 6.9.

6. A process according to claim 1, characterized in that the biomass obtained is filtered off from the nutrient solution after cultivation is completed.

* * * * *